(12) United States Patent
Jay (10) Patent No.: US 7,217,267 B2
(45) Date of Patent: May 15, 2007

(54) HAIR TREATMENT METHOD

(76) Inventor: Harvey Jay, 14 Cayuga Rd., Scarsdale, NY (US) 10583

( * ) Notice: Subject to any disclaimer, the term of this patent is extended or adjusted under 35 U.S.C. 154(b) by 183 days.

(21) Appl. No.: 10/773,621

(22) Filed: Feb. 6, 2004

(65) Prior Publication Data

US 2005/0049657 A1 Mar. 3, 2005

Related U.S. Application Data

(63) Continuation-in-part of application No. 10/647,948, filed on Aug. 26, 2003.

(51) Int. Cl.
*A61B 18/20* (2006.01)

(52) U.S. Cl. .......................... 606/18; 128/898; 606/9; 606/17

(58) Field of Classification Search ............... 128/898; 607/88–94; 606/9–18
See application file for complete search history.

(56) References Cited

U.S. PATENT DOCUMENTS

| | | | |
|---|---|---|---|
| 4,608,978 A * | 9/1986 | Rohr | 606/9 |
| 4,819,669 A * | 4/1989 | Politzer | 132/200 |
| 5,425,728 A | 6/1995 | Tankovich | |
| 5,533,266 A * | 7/1996 | Kelman | 30/122 |
| 5,595,568 A | 1/1997 | Anderson et al. | |
| 5,606,798 A * | 3/1997 | Kelman | 30/41.5 |
| 5,683,380 A | 11/1997 | Eckhouse et al. | |
| 5,707,403 A * | 1/1998 | Grove et al. | 607/89 |
| 5,735,844 A | 4/1998 | Anderson et al. | |
| 5,849,029 A | 12/1998 | Eckhouse et al. | |
| 5,885,273 A | 3/1999 | Eckhouse et al. | |
| 5,895,568 A | 4/1999 | Koltunov | |
| 5,916,211 A * | 6/1999 | Quon et al. | 606/9 |
| 5,993,440 A * | 11/1999 | Ghassemi | 606/9 |
| 6,050,990 A | 4/2000 | Tankovich et al. | |
| 6,063,076 A | 5/2000 | Mehl, Sr. et al. | |
| 6,152,917 A | 11/2000 | Tankovich | |
| 6,162,211 A * | 12/2000 | Tankovich et al. | 606/9 |
| 6,162,212 A | 12/2000 | Kreindel et al. | |
| 6,174,325 B1 | 1/2001 | Eckhouse et al. | |
| 6,228,074 B1 | 5/2001 | Almedia | |
| 6,267,771 B1 | 7/2001 | Tankovich et al. | |
| 6,280,438 B1 * | 8/2001 | Eckhouse et al. | 606/9 |
| 6,306,160 B1 * | 10/2001 | Nidetzky | 607/89 |
| 6,383,176 B1 | 5/2002 | Connors et al. | |
| 6,387,089 B1 | 5/2002 | Kreindel et al. | |
| 6,406,474 B1 | 6/2002 | Neuberger et al. | |
| 6,514,243 B1 * | 2/2003 | Eckhouse et al. | 606/9 |
| 6,533,775 B1 * | 3/2003 | Rizoiu | 606/9 |
| 6,663,659 B2 * | 12/2003 | McDaniel | 607/88 |
| 7,108,690 B1 * | 9/2006 | Lefki et al. | 606/10 |
| 2003/0011786 A1 * | 1/2003 | Levy et al. | 356/600 |

(Continued)

*Primary Examiner*—Henry M. Johnson, III
(74) *Attorney, Agent, or Firm*—R. Neil Sudol; Henry D. Coleman; William J. Sapone (57) ABSTRACT

A hair treatment device includes a generator of electromagnetic radiation and optical guide components operatively connected to the generator so as to direct electromagnetic radiation from the generator away from entering a skin surface and in a direction substantially parallel to the skin surface, to impinge on hair fibers protruding from the skin surface. A control unit is connected to the generator for controlling the generator to produce the electromagnetic radiation in bursts of light pulses each having a predetermined number of pulses of light for treating the hair fibers protruding from the skin surface.

13 Claims, 4 Drawing Sheets

U.S. PATENT DOCUMENTS

2003/0055414 A1* 3/2003 Altshuler et al. .............. 606/9
2003/0167033 A1* 9/2003 Chen et al. ................... 604/20
2004/0230260 A1* 11/2004 MacFarland et al. ......... 607/89
2006/0178659 A1* 8/2006 Van Hal et al. ................ 606/2

* cited by examiner

HAIR TREATMENT METHOD

CROSS-REFERENCE TO RELATED APPLICATION

This application is a continuation-in-part of application Ser. No. 10/647,948 filed Aug. 26, 2003.

BACKGROUND OF THE INVENTION

This invention relates generally to a hair treatment process. More particularly, this invention relates to a method for the temporary removal of hair and for the retardation of hair growth.

As discussed in U.S. Pat. No. 6,280,438, hair may be removed from selected skin surfaces by the application of intense, wide area, pulsed electromagnetic (light) energy.

According to the methodology of U.S. Pat. No. 6,280,438, the energy heats the hair and coagulates the tissue around the hair and follicle without damaging the healthy skin. Pursuant to that prior art disclosure, it is preferable to provide an optically transparent water based gel on the skin prior to treatment with the electromagnetic energy. The gel cools the epidermis but is applied so as not to enter the cavity around the hair follicle, and thus does not cool the hair and the hair follicle. The applied energy then coagulates the hair without damaging the skin.

U.S. Pat. No. 6,280,438 teaches the use of incoherent polychromatic radiation in a wavelength range that penetrates into the skin without being highly attenuated. It is indicated in the patent that wavelengths shorter than 550 nm are not useful because they will be highly attenuated before reaching the lower parts of the hair follicles. Instead, wavelengths in the range of 550 to 630 nm are heavily absorbed by blood and can therefore be used to coagulate the vessels that feed the hairs. Additionally, longer wavelengths, in the range of 600 to 1100 nm have a very good penetration into non-pigmented skin and can be used to couple to the melanin of the hair.

U.S. Pat. No. 5,885,273 discloses a method of removing hair that includes producing a plurality of pulses of incoherent electromagnetic energy, which is filtered in accordance with the color of the hair being removed. A flashlamp produces pulses having delays on the order of 0.1 msec to 100 msec, and an energy fluence on the order of 10 to 100 $J/cm^2$. Energy that has a wavelength of less than 500 nm or 600 nm and greater than 1300 nm is preferably filtered out. Light is applied to the treated area in either a long pulse or in a sequence of pulses separated by a delay. The delay and/or pulse length is preferably controlled by the operator to provide enough heat to remove the hair but not enough heat to damage the skin. For example, the pulse length or delay between the pulses should be more than the cooling time of the gel-covered epidermis and less than the cooling time of the hair and follicle. Specifically, a pulse length of 50 msec if a single pulse is used or a delay of 50 msec between the pulses if a pulse sequence is used are appropriate values.

In brief, the art using electromagnetic radiation such as pulses of incoherent light is intended to permanently remove hair from selected skin surfaces. The light pulses have parameters such as spectral dispersion, pulse duration and total energy that are, selected to destroy the hair follicles in the selected skin area. Understandably, such methods carry a certain amount of risk that the skin may be damaged. Accordingly, the prior art methods of hair depilation are typically intended for use by trained cosmetologists and other professionals. The consuming public is left with few options in removing undesired hair.

OBJECTS OF THE INVENTION

An object of the present invention is to provide a method for treating hair to at least retard hair growth.

It is a related object of the present invention to provide a method for temporary hair removal.

A more particular object of the present invention is to provide such a method of hair treatment or removal that is safe for home use.

It is a related object of the invention to provide a method for hair treatment, which may replace current home-based methods, for instance, of shaving, waxing, plucking, tweezing, or using depilatories.

A further object of the present invention is to provide such a treatment method that can result in a smooth cleaner hair removal than is possible with razors and shavers.

These and other objects of the present invention will be apparent from the drawings and descriptions herein. It is to be understood that each object of the invention is achieved by at least one embodiment of the invention. It is not necessarily the case that any embodiment achieves all of the objects of the invention.

SUMMARY OF THE INVENTION

A hair treatment device comprises, in accordance with the present invention, a generator of electromagnetic radiation and optical guide componentry operatively connected to the generator so as to direct electromagnetic radiation from the generator away from entering a skin surface and in a direction substantially parallel to the skin surface, to impinge on hair fibers protruding from the skin surface.

A control unit is preferably operatively connected to the generator for controlling the generator to produce the electromagnetic radiation in bursts of light pulses each having a predetermined number of pulses of light for treating the hair fibers protruding from the skin surface.

The hair fibers targeted by the optical guide componentry with electromagnetic radiation from the generator protrude from a measurable area of the skin surface. Pursuant to another feature of the present invention, the pulses of each of the radiation bursts have a total energy between approximately 0.1 Joule and approximately 100 Joules per square centimeter of the skin surface. Thus, where the hair treatment device is adapted to apply radiation to hair fibers located on a 0.2 square centimeter area of the skin surface, the hairs in that area are subjected to a total energy of between 0.02 Joule and 20 Joules. Generally, larger amounts of radiation are used where the target hair is light (blond, gray), coarse and dense. Conversely, lower amounts of radiation are used where the target hair is dark (black, brown), fine, and sparse.

Pursuant to an additional feature of the present invention, the pulses of light have a total duration between approximately 1 nanosecond and approximately 3 seconds. Each pulse of a multiple pulse burst of radiation may have durations between 1 nanosecond and 3 seconds. Generally, the longer durations are associated with light of reduced intensity, whereas the pulses of shorter durations are high intensity pulses. However, the rate that energy is delivered to the hair fibers varies in accordance with the desired effect. Generally, higher rates of energy delivery result in sharp cuts above the skin line, while lower rates of energy delivery result in hair damage along extended segments of the treated hairs including portions below the skin line. The latter kind of treatment can result in a closer kind of light-mediated "shave" insofar as hair severing can occur below the skin line.

Pursuant to further features of the present invention, the light of the pulses is incoherent and includes a range of wavelengths between about approximately 200 nm and approximately 1200 nm. This spectral range is particularly effective where the light is absorbed by melanin that is naturally occurring in the hair fibers. This spectral range may also be effective for some artificial dyes that may be applied to the hair fibers prior to the application of the pulsed light energy. Alternatively, the light of the pulses is incoherent and includes a range of wavelengths longer than about approximately 800 nm, for instance, in a range of 800 nm to 5000 nm. Light of this spectral range is absorbed by water in the hair fibers.

In an embodiment of the present invention, the generator and the optical guide componentry are mounted to a casing, which defines a light application chamber receiving the hair fibers protruding from the skin surface. The casing is preferably provided with light-absorbing shielding to prevent leakage of electromagnetic radiation from the chamber.

In accordance with another aspect of the present invention, at least one sensor is mounted to the casing for detecting engagement of the casing with the skin surface about the chamber. The sensor is operatively connected to the control unit for informing the control unit as to a state of engagement of the casing with the skin surface. The control unit interrupts production of the electromagnetic radiation in the event that the sensor indicates the possibility of radiation leakage.

In a particular embodiment of the present invention, the hair treatment chamber has a small opening such as a slit (e.g., 1 millimeter wide) through which hairs protrude from the skin surface. The device may have an element for inducing the hair to protrude through the opening and into the chamber, i.e., a hair elevation element may be mounted to the casing for inducing hair on the skin surface to stand away from the skin surface. The hair elevation element may be a suction source; a vibrator mechanism; a magnetizer assembly, or an assembly for the application of electrostatic charge. A magnetizer assembly includes an electromagnet and a device for applying a magnetic composition to hair on the skin surface, while an assembly for the application of electrostatic charge includes a charge generator for investing a flowable composition with an electric charge and a dispenser for applying the charged composition to hair on the skin surface.

The optical guide componentry may include one or more conventional light guiding elements such as mirrors, prisms, lenses, optical fibers, etc.

In accordance with a further aspect of the present invention, the control unit is operatively connected to the generator for inducing the generator to produce one or two kinds of temporally spaced bursts of electromagnetic radiation. One such burst has characteristic parameters including a spectral composition, intensity, and pulse duration effective to sever the hair shafts above the skin surface. Another such burst has characteristic parameters including a spectral composition, intensity, and pulse duration effective to generate, in hair shafts protruding from the skin surface, heat energy transmissible along the hair shafts to weaken the same below the skin surface and eventually result in severing the hairs below the skin surface. Where both kinds of radiation burst are used in the same hair treatment session, the hair is removed immediately, but the removal last longer than a convention razor-mediated shave since hair fibers are compromised (severed, weakened, damaged) below the skin surface.

A hair treatment device in accordance with the present invention may further comprise a reservoir of dye in the casing and a dispenser mounted to the casing. The dispenser is in communication with the reservoir for applying the dye to hairs along the skin surface prior to an application of electromagnetic radiation to the hairs via the optical guide componentry.

A hair treatment method comprises, in accordance with the present invention, generating electromagnetic radiation having a predetermined spectral composition and a predetermined intensity in a predetermined number of light pulses each having a predetermined duration, the light pulses having a predetermined total energy. The method further comprises directing the generated light pulses from the generator away from entering a skin surface and in a direction substantially parallel to the skin surface, to impinge on hair fibers protruding from the skin surface. The total energy of the pulses is between approximately 0.1 Joule and approximately 100 Joules of energy per square centimeter of the skin surface. The actual energy of a light pulse sequence depends on several factors, including the desired effect (immediate cutting above the skin line, eventual severing below the skin line), the number of hairs treated by the light pulse sequence (hair density and beam width), the effective color of the hair, and the thickness of the hair fibers. The effective color of hair may be affected by the application of a dye.

As discussed above with reference to a device for performing the method of the present invention, the pulses of light have a total duration between approximately 1 nanosecond and approximately 3 seconds. The light of the pulses is preferably incoherent (although laser light could be used) and includes a range of wavelengths between about approximately 200 nm and approximately 1200 nm where the primary absorber is melanin or an external chromophore (dye). Where the primary absorber is water, the light of the pulses includes a range of wavelengths longer than about approximately 800 nm.

The method may include delivering a second form of energy to the hair fibers to cause the fibers to stand away from the skin surface. The energy may be mechanical as in the case of suction or vibration, magnetic, or electrostatic.

As further discussed above, the light pulses may include a burst of electromagnetic radiation having characteristic parameters including a spectral composition, intensity, and pulse duration effective to generate, in hair shafts protruding from the skin surface, heat energy transmissible along the hair shafts to weaken the same below the skin surface. Alternatively or additionally, the light pulses may include radiation having characteristic parameters including a spectral composition, intensity, and pulse duration effective to sever the hair shafts above the skin surface.

The present invention provides a device and an associated method for treating hair, which cuts hair above the skin line, and/or retards hair growth. The device and method minimize skin irritation and trauma and result in a shave that is closer than that possible by conventional blades or electric razors. In addition, treatment of hair pursuant to the present invention avoids the transmission of light energy into the skin, thus reducing, if not eliminating, the risk of skin damage.

Accordingly, the present method of hair treatment is an attractive substitute for current home-based methods, for instance, of shaving, waxing, plucking, tweezing, or using depilatories.

DETAILED DESCRIPTION OF THE PREFERRED EMBODIMENTS

Figure 1:
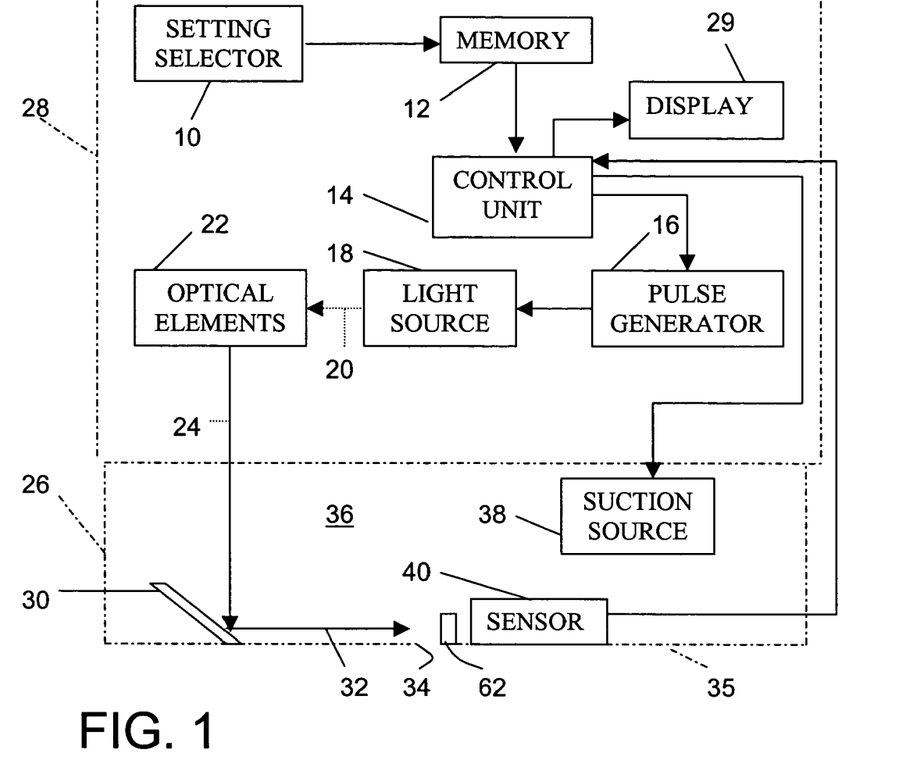
FIG. 1 is a block diagram of a light-pulse generating device in accordance with the present invention.

As depicted in FIG. 1, a device for generating light pulses for application to hair fibers protruding from a skin surface includes a manually operable setting selector 10 connected at an output to a memory 12 in turn connected at an output to a control unit 14. Memory 12 stores pre-established combinations of light pulse parameters including pulse width or duration, inter-pulse interval or delay time, pulse number, light intensity, and total treatment energy. Control unit 14 may be a microprocessor or a special logic circuit connected to a pulse generator 16 for inducing the generator to produce a sequence of electrical control pulses fed to a generator or source 18 of incoherent light energy. Source 18 produces light with a spectral distribution including wavelengths between 200 nm and 1200 nm, for absorption by melanin in the hair fibers or by a dye applied to the hair fibers (see FIG. 5). Alternatively, the light of the pulses includes a range of wavelengths longer than about approximately 800 nm, for instance, in a range of 800 nm to 5000 nm. Light of this spectral range is absorbed by water in the hair fibers. Control unit 14 may be connected directly to source 18 where the source incorporates means for varying pulse parameters pursuant to encoded instructions from the control unit.

Light generator or source 18 (as well as the entire light pulse applicator) may take any known form such as those disclosed in U.S. Pat. No. 6,280,438 and U.S. Pat. No. 5,885,273. Thus, light source 18 may be a Xenon flashlamp.

Light 20 generated by source 18 is directed through an array of optical elements 22 that may include one or more reflectors, lenses, and filters (not separately shown). Where an adjustable filter is included, control unit 14 may be connected to the filter for operatively modifying the action thereof. For instance, in the case of an adjustable neutral density filter, control unit 14 may induce a change in the filter density to control the intensity, and therefore the power, of the light applied to a selected skin surface.

In the case of multiple wavelengths of light being produced, an adjustable filter may be included in the optical elements 22 and/or an applicator or interface component 26. These filters can block undesired wavelengths and allow desired wavelengths to pass. Low end filters that block lower or shorter wavelengths, high end filters that block higher or longer wavelengths or band pass filters that block some high or some low end wavelengths may be utilized.

Light 24 leaving the optical array 22 is delivered or applied to hair fibers above a skin line via applicator or interface component 26, which may take the form of a cartridge removably attachable to a casing 28 of the light pulse generating device.

In contrast to light-based hair and/or skin treatment devices currently on the market, such as those disclosed in U.S. Pat. No. 6,280,438 and U.S. Pat. No. 5,885,273, the device and associated hair treatment method disclosed herein do not direct light into the skin and therefore do not require skin cooling. However, the device disclosed herein may include, as an optional feature, a nozzle or sprayer for applying coolant, a lubricating composition, a medication, or other fluid substance onto the skin. In that case, the light application device is provided with a reservoir of fluid, an ejection mechanism or pump, and a nozzle.

The elements of FIG. 1 are encased in or mounted to housing or casing 28, which may have a size and configuration enabling the pulse generation device to be hand held and easily manipulated for purposes of optically treating different skin surfaces of the individual user.

The device of FIG. 1 is preprogrammed to produce light pulses in any of several settings, each setting being defined by a respective combination of particular operational parameters including pulse duration, inter-pulse interval, pulse number, and intensity or total energy. For instance, the device may have several settings, for instance, high, medium, and low, which vary in the number of applied pulses, the pulse duration, the inter-pulse interval, and/or the total energy applied. Generally, the high setting is used for light, coarse and/or dense hair and the low setting is used for dark, fine, and/or sparse hair. The medium setting is used for hair having intermediate characteristics, such as a medium dark color, a medium thickness, and a moderate density on the skin surface. The number of pulses may vary between 1 and 3 or 4 or more. The pulse duration may vary from 1 nanosecond to 3 seconds. The inter-pulse interval (in the case of more than one pulse) may vary from 1 nanosecond to 3 seconds. The total energy applied may vary from 0.1 Joule per square centimeter of skin surface to 100 Joules per square centimeter of skin surface.

A user of the device of FIG. 1 would generally start with a low setting to see whether the hair falls out or is cut and if not, try the next higher setting. Usually, it is preferable to use the lowest setting which accomplishes the desired result.

Applicator or interface component 26 includes one or more optical guide elements such as a mirror 30 operatively connected to light source 18 via optical elements 22 so as to direct electromagnetic radiation from the light source away from entering a skin surface and in a direction 32 substantially parallel to the skin surface, to impinge on hair fibers protruding from the skin surface through an opening 34 in a skin-engaging contact panel 35 of applicator or interface component 26.

Applicator or interface component 26 includes a casing or housing (not separately designated) that may be considered part of casing 28 and that defines a light application or hair treatment chamber 36 communicating with opening 34. Applicator or interface component 26 contains a suction source 38 for depressurizing treatment chamber 36 and inducing hair fibers to stand straight up from an underlying hair surface into the chamber via opening 34. Applicator or interface component 26 may be additionally provided with a sensor 40 such as a microswitch, a voltage meter or electric potential detector, etc., for determining whether panel 35 is in contact with an underlying skin surface so that opening 34 may receive hairs protruding from the skin surface. Sensor 40 is connected to control unit 14 which in turn is connected to suction source 38. Control unit 14 de-activates generator or light source 18 in the event that sensor 40 detects a disengagement of panel 35 from the underlying skin surface. Control unit 14 may also de-energize suction source 38 upon detecting such a disengagement.

Figure 2:
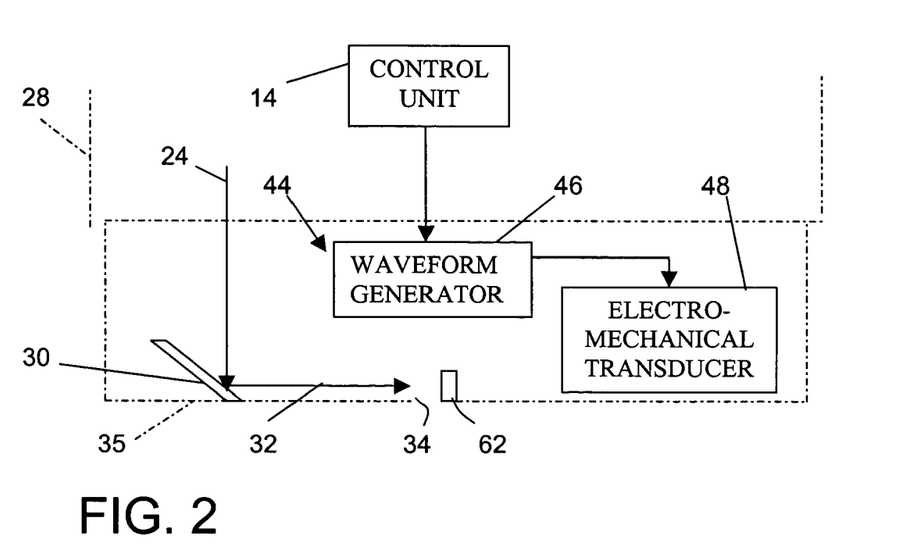
FIG. 2 is a block diagram showing a first modification of the device of FIG. 1.

FIG. 2 illustrates an alternative to suction source 38 (FIG. 1) as a hair elevation element for inducing hair to stand away from the skin surface and protrude through opening 34 and into the chamber 36. In particular, control unit 14 is operatively connected to a vibrator mechanism 44 including a waveform generator 46 connected at an output to an electromechanical transducer 48 such as a piezoelectric crystal or a magnetic vibrator. Transducer 48 is positioned along panel 35 proximate to opening 34 to vibrate the skin surface and facilitate the extension of hairs into chamber 36.

Figure 3:
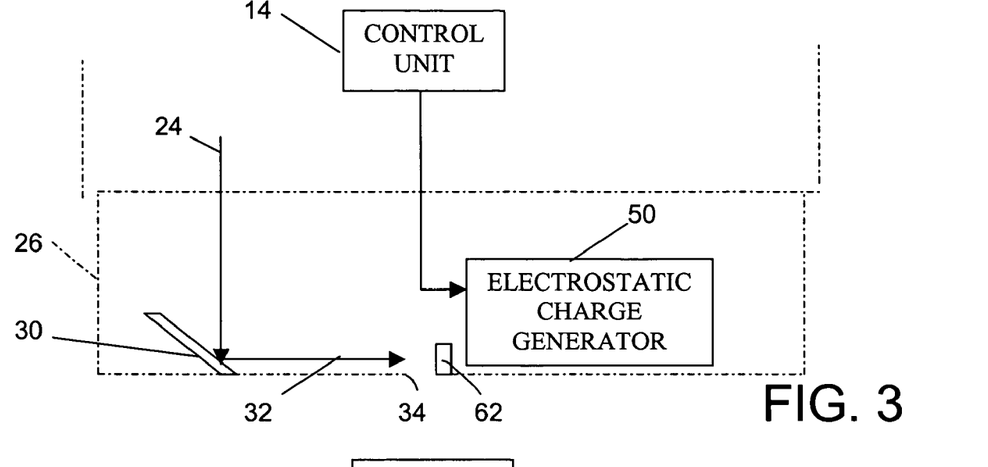
FIG. 3 is a block diagram showing a second modification of the device of FIG. 1.

FIG. 3 depicts another alternative to suction source 38 (FIG. 1) as a hair elevation element for inducing hair to stand away from the skin surface and protrude through opening 34 and into the chamber 36. In particular, control unit 14 is operatively connected to an electrostatic charge generator 50 that may dispense an electrostatically charged powder or other fluidic composition onto hair fibers and the respective skin surface, thereby causing the fibers to be repelled from the skin surface.

Figure 4:
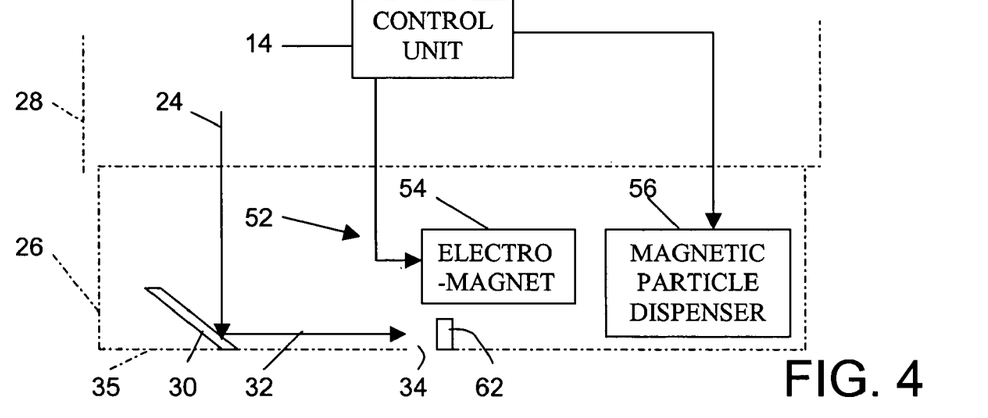
FIG. 4 is a block diagram showing a third modification of the device of FIG. 1.

As shown in FIG. 4, another alternative to suction source 38 (FIG. 1) takes the form of a magnetizer assembly 52 including an electromagnet 54 and a dispenser 56 for applying a magnetic composition to hair on the skin surface. Control unit 14 is operatively connected to electromagnet 54 and dispenser 56 for operating same when panel 35 is in effective contact with an underlying skin surface.

Figure 5:
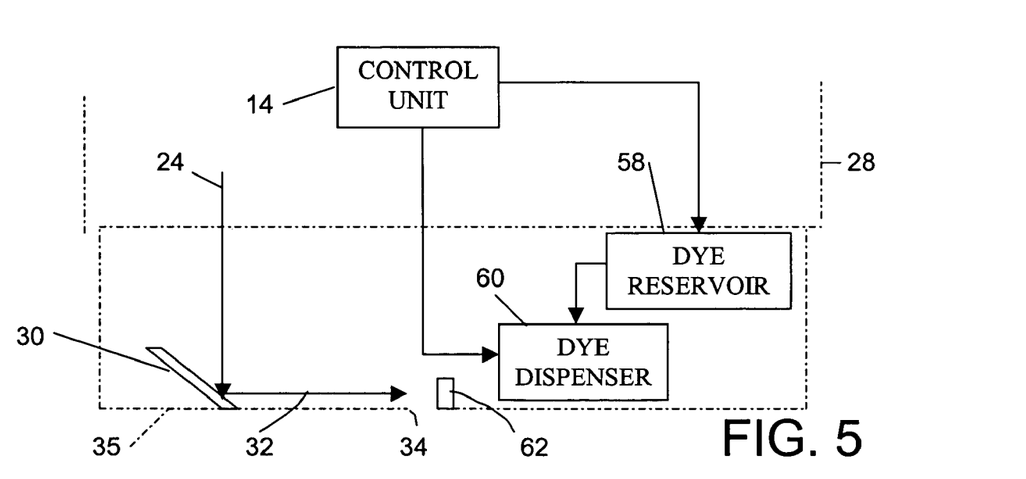
FIG. 5 is a block diagram showing a fourth modification of the device of FIG. 1.

As illustrated in FIG. 5, the light application or hair treatment device of FIG. 1 (or FIGS. 2–4) may be provided with a dye reservoir 58 and a dye dispenser 60 operatively connected to control unit 14 for applying an external chromophore to hair fibers along the skin surface. Preferably, the dye is water soluble or otherwise easily removed by soap and water.

Applicator or interface component 26 is provided with shielding, for instance, a layer of light absorbing material (not separately designated) coating the inside surfaces of chamber 36. Alternatively or additionally, applicator or interface component 26 is provided with shielding in the form of light-absorbing strips 62 disposed along opening 34 for absorbing any light that is not absorbed by hair fibers protruding through opening 34 into chamber 36.

Control unit 14 may be programmed for inducing generator or light source 14 to produce either one or both of two kinds of temporally spaced bursts of electromagnetic radiation. One such burst has characteristic parameters including a spectral composition, intensity, and pulse duration effective to sever the hair shafts above the skin surface. Another such burst has characteristic parameters including a spectral composition, intensity, and pulse duration effective to generate, in hair shafts protruding from the skin surface, heat energy transmissible along the hair shafts to weaken the same below the skin surface and eventually result in severing the hairs below the skin surface. Where both kinds of radiation burst are used in the same hair treatment session, the hair is removed immediately, but the removal last longer than a convention razor-mediated shave since hair fibers are compromised (severed, weakened, damaged) below the skin surface.

During use of the light application or hair treatment device of FIG. 1 at any of the pre-established treatment settings, control unit 14 causes light generator 18 and optical elements 22 to generate electromagnetic radiation 24 having a respective spectral composition and a respective intensity in a respective number of light pulses each having a respective duration, the light pulses having a predetermined total energy. Mirror 30 (together with optical elements 22) directs the generated light pulses away from entering a skin surface and in direction 32 substantially parallel to the skin surface, to impinge on hair fibers protruding from the skin surface through opening 34 into chamber 36. The total energy of the pulses is between approximately 0.1 Joule and 1 Joule for the lowest setting, between 1 Joule and 20 Joules for the middle setting, and between 20 Joules and approximately 100 Joules of energy per square centimeter of the skin surface for the highest setting.

Upon contact of panel 35 with the skin surface, as determined by sensor 40, control unit 14 causes a second form of energy to be emitted to cause the hair fibers to stand away from the skin surface. The energy may be mechanical as in the case of suction (FIG. 1) or vibration (FIG. 2), electrostatic (FIG. 3), or magnetic (FIG. 4).

The device of FIG. 1 may be provided with additional settings (for instance, high, medium, and low hair growth reduction settings) where in addition to a set of pulses for cutting the hair fibers above the skin line, a set of pulses are emitted with a spectral composition, intensity, and pulse duration effective to generate, in hair shafts protruding from the skin surface, heat energy transmissible along the hair shafts to weaken the same below the skin surface. Thus, the light-mediated shave enables the user to wait a longer period between successive hair treatments, since the hairs become weakened and then severed below the skin line.

The device of FIG. 1 is preprogrammed to produce light pulses in any of several settings, each setting being defined by a respective combination of particular operational parameters including pulse duration, inter-pulse interval, pulse number, and intensity or total energy. For instance, the device may have several settings, for instance, high, medium, and low, which vary in the number of applied pulses, the pulse duration, the inter-pulse interval, and/or the total energy applied. Generally, the high setting is used for light, coarse and/or dense hair and the low setting is used for dark, fine, and/or sparse hair. The medium setting is used for hair having intermediate characteristics, such as a medium dark color, a medium thickness, and a moderate density on the skin surface. The number of pulses may vary between 1 and 3 or 4 or more. The pulse duration may vary from 1 nanosecond to 3 seconds. The inter-pulse interval (in the case of more than one pulse) may vary from 1 nanosecond to 3 seconds. The total energy applied may vary from 0.1 Joule per square centimeter of skin surface to 100 Joules per square centimeter of skin surface.

Figure 6:
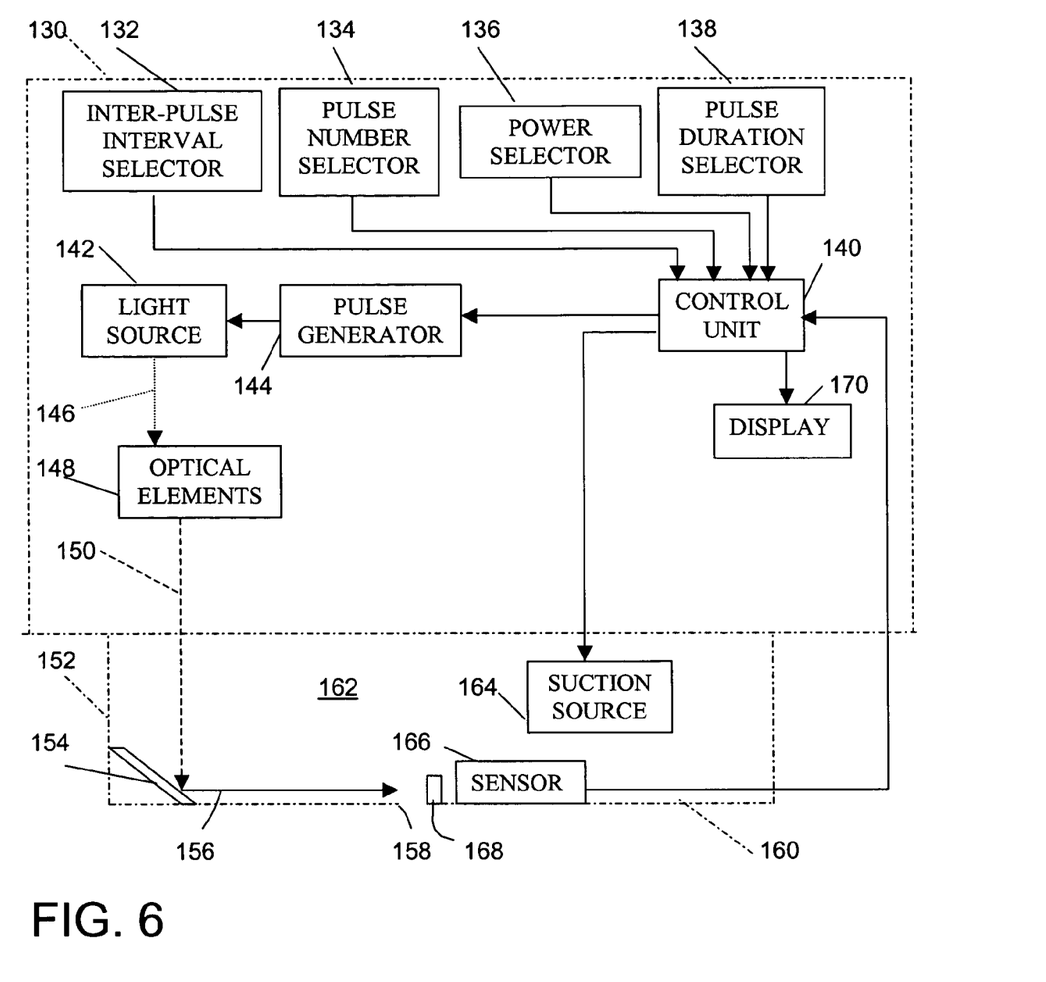
FIG. 6 is a block diagram of another light pulse generating device in accordance with the present invention.

A more advanced or complex device is illustrated in FIG. 6. This device includes a housing or casing 130 having manually actuatable input elements 132, 134, 136, and 138, such as rotary knobs or a solid-state touch screen, which enable a user to individually select multiple operating parameters. Input elements or selectors 132, 134, 136, and 138 are an inter-pulse interval selector, a pulse number selector, a power or energy selector, and a pulse duration selection, respectively. Another selector (not shown) could be for intensity adjustment, while a further selector may be provided for adjusting a light source 142 or a filter in optical elements 148 and/or an applicator or interface component 152 for modifying the wavelength band delivered to the target hair fibers. Selectors 132, 134, 136, and 138 are operatively tied to a control unit 140 such as a microprocessor or hard-wired log circuit. Control unit 140 regulates the operation of light source 142 such as a conventional flashlamp, either directly or indirectly via a pulse generator

144. Light 146 from source 142 is transmitted along a path through optical elements 148 optionally including one or more reflectors, lenses, and filters (not separately shown). Light 150 at an output of the optical array 148 is applied via applicator or interface component 152 to segments of hair fibers protruding above a skin surface.

Applicator or interface component 152 takes the structure of applicator or interface component 26, as described above with reference to the embodiments of FIGS. 1–5. In particular, as shown in FIG. 6, applicator or interface component 126 includes one or more optical guide elements such as a mirror 154 operatively connected to light source 142 via optical elements 148 so as to direct electromagnetic radiation from the light source away from entering a skin surface and in a direction 156 substantially parallel to the skin surface, to impinge on hair fibers protruding from the skin surface through an opening 158 in a skin-engaging contact panel 160 of applicator or interface component 152.

Applicator or interface component 152 includes a casing or housing (not separately designated) that may be considered part of casing 130 and that defines a light application or hair treatment chamber 162 communicating with opening 158. Applicator or interface component 152 contains a suction source 164 for depressurizing treatment chamber 162 and inducing hair fibers to stand straight up from an underlying hair surface into the chamber via opening 158. Applicator or interface component 152 may be additionally provided with a sensor 166 such as a microswitch, a voltage meter or electric potential detector, etc., for determining whether panel 160 is in contact with an underlying skin surface so that opening 158 may receive hairs protruding from the skin surface. Sensor 166 is connected to control unit 140, which in turn is connected to suction source 164. Control unit 140 de-activates generator or light source 142 in the event that sensor 166 detects a disengagement of panel 160 from the underlying skin surface. Control unit 140 may also de-energize suction source 164 upon detecting such a disengagement.

Applicator or interface component 152 is provided with shielding for inhibiting or preventing the leakage of light energy from chamber 162. To that end, chamber 162 may be lined with a layer of light-absorbing material (e.g., black paint). Alternatively or additionally, applicator or interface component 152 is provided with shielding in the form of light-absorbing strips 168 disposed along opening 158 for absorbing any light that is not absorbed by hair fibers protruding through opening 158 into chamber 162.

The device of FIG. 6 may be provided with a display 170 for providing information to a user. Such information may include numerical values of various pulse parameters set by the user's manipulation of input elements or selectors 132, 134, 136, and 138. The displayed information may also include feedback such as preprogrammed limitations on pulse parameter ranges, instructions as to device use, and recommendations as to pulse parameter values. The device of FIG. 6 may also include a keyboard or other input element (not illustrated) for enabling the user to record pulse parameter settings, to request instructions and recommendations, etc.

In one embodiment of the device of FIG. 6, inter-pulse interval selector 132 provides for intervals in a range from 1 nanosecond (nsec) to 3 seconds, whereas pulse number selector 134 is enabled for pulse sequences of one to ten pulses. In addition, power selector 136 permits treatment energies between 0.1 Joule per square centimeter of skin surface and 100 Joules per square centimeter, while pulse duration selector 138 enables pulses of 1 nsec to 3 seconds in length. Total pulse sequence duration, from the beginning of the first pulse to the termination of the final pulse, ranges from 1 nsec to 3 seconds. The various pulse sequence parameters may be selectable from sets of discrete values or, alternatively, from continuous ranges.

In the device of FIG. 6, the various parameters are typically not completely independent inasmuch as the total energy selected will function as a constraint on the ranges available for the other parameters, that is, the total energy selected will serve to regulate or circumscribe the ranges available to the user for the other pulse sequence parameters. Where the device of FIG. 6 has no intensity adjustment capability, a selection of the total energy and the pulse duration may determine the number of pulses. Similarly, a selection of the total energy and the number of pulses may determine the pulse duration. If the intensity is an adjustable parameter, once the total energy has been chosen, the user will be able to select the magnitudes of two of the three parameters, pulse duration, intensity and number of pulses. The inter-pulse interval is related to the rate at which radiant energy is applied to a skin surface and may accordingly be subjected to some programmed control. Longer pulse durations and/or delays will deliver energy at a slower rate (total energy is distributed over longer time) and therefore be safer to use with higher energy levels. Preferably, the total energy is always a selectable parameter and is best selected prior to the setting of the other parameters. However, the device of FIG. 6 may be preprogrammed to limit the rate at which radiant energy is applied to hair fibers, which will force restrictions on the user's ability to select pulse parameter values.

In an alternative embodiment of the device of FIG. 6, particularly suitable for home use, inter-pulse interval selector 132 enables a selection of intervals ranging from 0.1 nsec to 2 seconds, while power selector 136 enables treatment energies between 0.1 $J/cm^2$ and 40 $J/cm^2$. Preferably, the pulse duration and the number of pulses available for selection are restricted so as to prevent the user from delivering energy at too high a rate. If the user selects a large pulse number, the pulse duration is necessarily short, whereas a small number of pulses forces a longer pulse duration in order to achieve the selected total energy. It is preferable to use a larger number of pulses and a smaller pulse duration in order to limit the rate at which light energy is applied to protruding hair fibers. Pulse number selector 134 may therefore enable a selection of three to ten pulses per pulse sequence, while pulse duration selector 138 enables a selection of pulses lasting 1 msec to 10 msec. The various pulse sequence parameters may be selectable from sets of discrete values or, alternatively, from continuous ranges.

As indicated above, a person may use the device of FIG. 6 (or a properly preprogrammed device as in FIG. 1) to apply pulses of light to protruding hair fibers for purposes of heat damaging and effectively severing the hair fibers below the surface of the skin to temporarily prevent hairs from growing through and thus becoming visible on the skin. The user first performs a calibration or initialization procedure to determine an appropriate pulse setting and a hair-regeneration period for that setting. The term "hair-regeneration period" is used herein to denote the time it takes for hair to reappear on the skin surface after a pulse sequence has been applied to protruding hair fibers at a selected setting.

As discussed above, control unit 140 activates light source 142 to produce light pulses in bursts having a total energy between approximately 0.1 Joule and approximately 100 Joules per square centimeter of the skin surface. If opening 158 takes the form of a slit one-half millimeter wide and two centimeters long, hairs pulled into chamber 162 through opening 158 are collectively subjected to an energy of between 0.01 Joule and 10 Joules. Generally, stronger doses of radiation are used where the target hair is light hued, coarse and dense, while weaker does are used where the target hair is dark, fine, and sparse.

As further discussed above, the radiation pulses in a particular burst have a total duration between approximately 1 nanosecond and approximately 3 seconds. Each pulse may have a duration between 1 nanosecond and 3 seconds. An inter-pulse interval, in the case of a multiple-pulse burst, may likewise have a length between 1 nanosecond and 3 seconds.

Using the device of FIG. 6, a user can select the parameters of two or more distinct pulse sequences to be delivered to each group of hair fibers captured via opening 158. One pulse sequence may define a relatively low rate of energy application, for inducing heat conduction along the hair fibers to segments thereof below the skin line, while another pulse sequence may define a relatively high rate of energy application, for sharply severing the hair above the skin line. Generally, pulse sequences for damaging (and ultimately severing) hair fibers below the skin line are characterized by low light intensities, long pulse durations, long inter-pulse intervals, and low total energies. Conversely, pulse sequences for sharply severing hair fibers above the skin line are characterized by high light intensities, short pulse durations, short inter-pulse intervals, and large amounts of total energy.

Where a user is interested in applying two pulse sequences to hair on a given area of skin, a calibration or initialization procedure may be carried out to determine optimal pulse parameter settings for each pulse sequence. For instance, the user may first select a low-energy pulse sequence to determine whether that sequence is effective in severing hair above the skin line. If the individual finds that a given setting does not immediately cut the hair, the individual should retry the calibration or initialization procedure using a higher-energy setting. Once the lowest energy setting is found for cutting the hairs, a further calibration or initialization procedure may be carried out to determine the optimal parameters for convectively severing the hair below the skin line. The user may wish to wait until hair growth has regenerated the hair on the target skin surface. Pulse parameters having a low rate of energy application are first selected. The individual may wait a day or so to see whether the hair falls out owing to the heat damage. If not, a different set of parameters is selected to deliver a greater burst of energy to the hair fibers. Once pulse parameters are discovered that result in the hair falling out owing to damage below the skin surface, the individual may begin to use the device of FIG. 2 on a regular or periodic basis to deliver two bursts of radiation as respective pulse sequences to hair fibers extending into chamber 162 via opening 158. The resulting light-mediated shave will be smoother and last longer than conventional razor or shaver cuts.

Using the device of FIG. 1 (or 2–4), an individual will first select a low setting to determine whether that low setting is effective in hair removal. If not, a next higher or medium setting may be tried. Generally, higher settings will be used only as the circumstances warrant, for instance, if the hair fibers are thick and the skin is light.

In determining optimal settings with the device of FIG. 6, a user should choose initial parameter values which in combination result in the application of small amounts of energy. Thus, where one or more selected pulse parameters are associated with high treatment energies, other pulse parameters should be selected that are associated with low treatment energies.

Generally, lower treatment energies are associated chiefly with lower total energies, say, from 0.1 Joules per square centimeter of skin surface to 10 Joules per square centimeter of skin surface. However, to ensure that the rate of energy application is low for any given total amount of light energy, the other pulse parameters must be selected properly. The energy should be delivered over a relatively long period, greater than one millisecond and up to 3 seconds. If there are multiple pulses in that time period, the individual pulses should have long durations, while the inter-pulse intervals should be short.

Conversely, higher treatment energies are associated chiefly with higher total energies, say, from 20 Joules per square centimeter of skin surface to 100 Joules per square centimeter of skin surface. To ensure that the rate of energy application is high for any given total amount of light energy, the other pulse parameters must be chosen judiciously. The energy should be delivered over a relatively short period, less than one millisecond and down to 1 nanosecond. If there are multiple pulses in that time period, the individual pulses should have short durations to increase the energy concentration during light delivery.

Where the instantaneous light intensity is held to a uniform value while the remaining pulse parameters are essentially independently adjustable, lower treatment energies will generally result from settings involving few pulses (say, 1–3 instead of 8–10 pulses), long inter-pulse intervals (300 msec or more), short pulse durations (20 msec or less). In these circumstances, the total energies will be relatively low, for instance, less than 10 or 20 Joules per square centimeter of skin surface. If a given setting proves to be ineffective at a given light intensity, the user might adjust selector 132 or 138 to decrease the inter-pulse interval or inefase decrease the pulse length, thereby effectively increasing the average power or rate at which the radiant energy is delivered to the target skin surface. Alternatively or additionally, the user might increase the number of pulses via selector 134.

Increasing the total applied energy via selector 136 while holding the other pulse parameters (except intensity) constant will generally result in a higher intensity and thus a higher rate of energy delivery and a greater chance of hair fiber cutting. If the light intensity is separately adjustable, one may increase the power or rate of energy delivery by simply selecting a higher intensity value.

Where the various pulse parameters are not independently selectable, for instance, where the total energy applied is a controlling factor, adjustments made in the parameters for purposes of incrementally enhancing the hair removal effectiveness of the device of FIG. 6 will be different from the case of completely independent parameter values. For instance, once the total applied energy and total pulse sequence time have been selected, decreasing the number of pulses will require an increase in pulse length and/or an increase in pulse intensity in order to deliver the same amount of total energy in the fixed time. These changes will increase the effectiveness of the light application inasmuch as the rate of energy delivery is increased. In contrast, once the total applied energy and total pulse sequence time have been selected, increasing the pulse duration will decrease the instantaneous rate at which energy is applied to protruding hair fibers of the target skin surface by decreasing the light intensity.

It is to be noted that hair growth rates vary from person to person and for different body locations on the same person. Therefore, the calibration procedure may require repeating on hair fibers of the different skin areas. Because different skin areas have different grades of hair (different colors, different fiber diameters, different hair densities) and different skin pigmentation, etc., different pulse parameter settings are recommended for different skin areas. For example, different settings will be necessary for the underarms and the legs in order to optimize results. In addition, hair treatment schedules may also vary from one skin area to another.

Where the user is applying light pulses to convectively destroy hair fiber below the skin surface, it may be found that hair regrowth slows down over time. In other words, the interval between reappearance of hair on a skin surface increases. For instance, it may happen determined that hair that reappeared on a leg within two weeks time may, after several months of light treatment as discussed herein, begin to reappear after three weeks after treatment with light at a given pulse sequence setting.

The present hair removal method accordingly contemplates the periodic application, to protruding hair fibers along a selected skin surface, of a pulse sequence having a predetermined number of pulses of light of a predetermined electromagnetic spectrum, a predetermined duration, a predetermined inter-pulse interval, and a predetermined total energy. These pulse sequence parameters are determined in part by the design of the light-generating device used and in part by the selections made by the user. The light treatment either cuts hair fibers above the skin line and/or temporarily prevents a growth of hair through the selected skin surface, depending on the amount and the rate of application of light energy to the protruding hair fibers.

The light of the pulses is generally incoherent and the spectrum includes wavelengths between about 200 nm and 1200 nm. This spectral range targets melanin in the hair fibers, as well as any dyes applied to the fibers (FIG. 5). In addition, wavelengths above 800 nm (e.g. between 800 nm and 1500 nm) will target water molecules in the hair. However, single wavelengths of laser or coherent light may be delivered at one time, when desired.

The light applied to a skin surface by the devices of FIGS. 1 and 6 includes at least one wavelength absorbable by an endogenous chromophore in a person's hair. The endogenous chromophore may be a form of melanin such as pheomelanin or eumelanin. In a more advanced embodiment the light application device may include a setting or control (not shown) for selecting a spectrum or range of wavelengths appropriate to the user's hair color. For instance, for lighter hair, the wavelengths selected encompass one or more natural absorption wavelengths of pheomelanin. For darker hair, the wavelengths selected encompass one or more natural absorption wavelengths of eumelanin. In any event, the devices of FIGS. 1 and 6 may be used with the application of an exogenous chromophore (dye) to the hair fibers for light absorption purposes.

In other embodiments of a light generation and application device for hair treatment, one or more of the pulse parameters may vary during a single treatment session. For instance, the inter-pulse interval or the pulse duration may increase or decrease from the beginning of a pulse sequence to the end of the pulse sequence. The resulting instantaneous rate of energy application may therefore vary during the pulse sequence.

Figure 7:
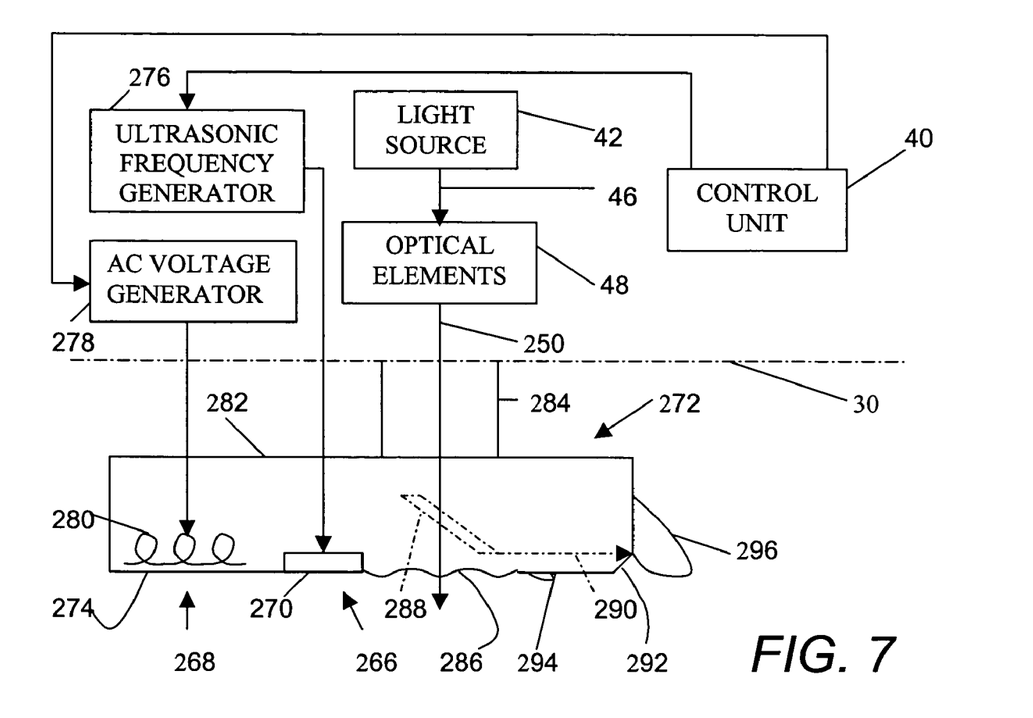
FIG. 7 is a partial block diagram of a light-pulse generating device including features representing a modification of the device of FIG. 1 or FIG. 2.

As depicted in FIG. 7, the light treatment devices of FIGS. 1 and 2 may incorporate a generator 266 of ultrasonic vibrations and/or an electromagnet 268 for enabling the application of ultrasound energy or a magnetic field (preferably oscillating) to a skin surface before, during or after the application of light energy to hair fibers. Permissible and recommended variations in the relevant parameters are well known in the skin treatment arts. In the case of ultrasound energy, one or more piezoelectric crystals 270 are disposed in or in contact with an applicator interface 272, e.g., a fluid-filled member having a flexible panel 274 for contacting and conforming to the skin surface. A waveform generator 276 transmits an ultrasonic-frequency electrical signal to the piezoelectric crystal(s) 270 for producing ultrasonic vibrations in skin tissues. An AC voltage generator 278 is operatively connected to an electromagnetic coil 280 for generating an alternating magnetic field in the skin tissues.

The applicator interface 272 of FIG. 7 includes an enlarged contact member or head 282 connected to the housing 28, 130 by a stem 284. Head 282 and optionally stem 284 are filled with a coolant fluid such as water or a gel. Prior to the use of the light-generating instrument, head 282 and optionally stem 284 may be stored in a refrigeration unit for purposes of reducing the temperature the water or gel. In that event, head 282 or stem 284 is provided with a connector (not shown) for detachably coupling the head or the stem to housing 28, 130. The connector includes electrical contacts (not shown) for the transmission of ultrasonic electrical waves from frequency generator 276 and another signal from AC voltage generator 278. In an alternative, more expensive embodiment of a light generating apparatus, the fluid in interface 272 may be circulated from a heat exchange unit (not shown) by a pump (not shown).

Applicator interface 272 has an opaque outer surface (not separately designated) except possibly along an area 286 of skin-contacting panel 274 opposite stem 284. Light 250 at an output of the optical array 48 is transmitted through stem 284, head 282, and transparent area 286.

As illustrated in FIG. 3, piezoelectric crystals 270 and coil 280 may be disposed inside head 282. Where the fluid is electrically conductive, crystals 270 and coil 280 are provided with appropriate electrical insulation such as a coating of a thermoplastic resin material. Alternatively, crystals 270 and coil 280 may be disposed inside housing 28 or 130. In that case, crystals 270 are in mechanical contact with stem 284 so as to enable the transmission of ultrasonic pressure waves through stem 284 and head 282 to panel 274. Electromagnetic coil 280 is of such as size that the magnetic field generated inside the dermal tissues is sufficiently large to effectively treat the skin tissues, in conjunction with the light treatment and optionally ultrasound.

As depicted in FIG. 7, head 282 is further provided with optics (e.g., a fully or optionally partially silvered mirror 288) for transmitting light 290 in a direction parallel to a skin surface. The light exits head 282 at a window 292 provided along a leading edge of the head for purposes of applying the light to hair protruding from the skin surface. The light 290 singes the hair which is then broken off by a bumper element 294 protruding slightly from a lower surface of panel 274. The removal of the hair enhances the effectiveness of the light penetration into the dermal tissues. A shield 296 may extend from the leading end of head 282 to block the escape of light 290 from a hair-treatment space immediately in advance of window 292.

Mirror 288 is tilted at an approximately 45° angle to the direction of transmission of light 250, i.e., at an approximately 45° angle to a perpendicular or normal to the skin surface.

Listed below are a number of exemplary settings or combinations of operational parameters attainable with either the device of FIG. 1 having pre-established settings or parameter combinations or the device of FIG. 6 where the various pulse sequence parameters may be individually adjusted independently of the other parameters. In these examples, the total times of the pulse sequences are determined by the selected numbers of pulses, the selected pulse durations and the selected inter-pulse intervals. The light intensity may be automatically adjusted by the light generating device if necessary to ensure consistency among the listed parameter settings.

EXAMPLE 1

In a preferred setting or combination of operational parameters, an incoherent light applicator device for severing hair fibers above a skin surface generates pulses with a pulse number of one, a pulse duration of 2 nanoseconds, a total pulse energy of 20 J/cm$^2$, and a spectral distribution of a commercially available flashlamp, including wavelengths between 200 and 1200 nm. This setting is very high, for severing light, coarse and dense hair fibers. The total energy can be increased, but it is generally not recommended.

EXAMPLE 2

A lower setting or combination of operational parameters involves a pulse sequence with a pulse number of two, a pulse duration of 20 nanoseconds, an inter-pulse interval of 1 msec, a total pulse energy of 20 J/cm$^2$, and a spectral distribution of a commercially available flashlamp, including wavelengths between 200 and 1200 nm. Even though the total energy is the same as in the first example, the energy is delivered over a longer period of time. Thus, the light intensity and the rate of energy application are lower. This setting is high, for severing fine light hair with a medium to heavy density.

EXAMPLE 3

A still lower setting or combination of operational parameters involves pulses with a pulse number of two, a pulse duration of 0.1 msec, an inter-pulse interval of 200 msec, a total pulse energy of 20 J/cm$^2$, and a spectral distribution of a commercially available flashlamp, including wavelengths between 200 and 1200 nm.

EXAMPLE 4

Another low setting or combination of operational parameters for an incoherent light applicator device involves pulses with a pulse number of two, a pulse duration of 0.1 msec, an inter-pulse interval of 200 msec, a total pulse energy of 10 J/cm$^2$, and a spectral distribution of a commercially available flashlamp, including wavelengths between 200 and 1200 nm. The pulse sequence of this example delivers a lower amount of radiant energy at a substantially reduced rate than in the third example. This setting is considered appropriate for cutting dark hair fibers that are coarse and dense.

The above examples provide possible settings for cutting hair fibers above the skin line. The following examples provide possible settings for damaging and severing hair fibers below the skin line, where heat conduction effectuates the damage.

EXAMPLE 5

In a very low setting or combination of operational parameters, an incoherent light applicator device produces pulses with a pulse number of four, a pulse duration of 200 msec msec, an inter-pulse interval of 200 msec, a total pulse energy of 1 J/cm$^2$, and a spectral distribution of a commercially available flashlamp, including wavelengths between 200 and 1200 nm. The pulse sequence of this example delivers a small amount of energy, at a low rate (e.g., long inter-pulse interval).

EXAMPLE 6

A slightly higher setting or combination of operational parameters for an incoherent light applicator device involves pulses with a pulse number of four, a pulse duration of 150 msec, an inter-pulse interval of 150 msec, a total pulse energy of 1 J/cm$^2$, and a spectral distribution of a commercially available flashlamp, including wavelengths between 200 and 1200 nm.

EXAMPLE 7

A still higher setting or combination of operational parameters for an incoherent light applicator device involves pulses with a pulse number of three, a pulse duration of 100 msec, an inter-pulse interval of 100 msec, a total pulse energy of 2 J/cm$^2$, and a spectral distribution of a commercially available flashlamp, including wavelengths between 200 and 1200 nm.

EXAMPLE 8

An even higher setting or combination of operational parameters for an incoherent light applicator device involves pulses with a pulse number of two, a pulse duration of 10 msec, an inter-pulse interval of 100 msec, a total pulse energy of 5 J/cm$^2$, and a spectral distribution of a commercially available flashlamp, including wavelengths between 200 and 1200 nm.

The devices of FIGS. 1 and 6 may be provided with a band-pass filter for limiting the spectral distribution of the generated light pulses to wavelengths in a given band, for instance, between 700 nm and 900 nm. Alternatively, a low-pass filter may be used for transmitting, to hair fibers, only wavelengths greater than a predetermined minimum, such as 800 nm.

Pulse sequences as listed above in examples 1–4 may be combined with pulse sequences listed in examples 5–8 to sever hair fibers both above the skin line and below. Such treatments result not only in instantaneous removal of hair above the skin line but also damages and effectively severs hair fibers below the skin line, thus resulting in smoother and longer lasting shaves.

It is to be noted that the hair treatment method described herein may include multiple passes over any particular skin surface. The selected light treatment parameters may be the same for each pass or may vary from pass to pass. In addition, the passes may follow immediately after one another or may be spaced by an interval during which, for instance, the light treatment device is used to apply light pulses to hair fibers along another area of the user's skin.

Although the invention has been described in terms of particular embodiments and applications, one of ordinary skill in the art, in light of this teaching, can generate additional embodiments and modifications without departing from the spirit of or exceeding the scope of the claimed invention. For example, light sources 18 and 142 may take the form of laser sources. In that case, if optical elements 22 and 148 include any filters, those filters are neutral density filters for reducing the intensity of the transmitted radiation. Where light sources 18 and 142 are tunable laser sources, then an additional actuator may be provided for frequency selection purposes.

A device in accordance with the present invention may cut hair through direct contact of an applicator element (e.g., a quartz crystal along opening 34 or 158) with hair fibers. Alternatively, only the light rays may contact the hair. Hair may be cut on a fiber-by-fiber basis or in clumps.

Accordingly, it is to be understood that the drawings and descriptions herein are proffered by way of example to facilitate comprehension of the invention and should not be construed to limit the scope thereof.

What is claimed is:

1. A hair treatment method comprising:
generating electromagnetic radiation having a predetermined spectral composition and a predetermined intensity in a predetermined number of pulses each having a predetermined duration, said pulses having a predetermined total energy; and
directing the generated pulses from said generator away from entering a skin surface and in a direction substantially parallel to said skin surface, to impinge on hair fibers protruding from the skin surface,
said pulses including at least two temporally spaced bursts of electromagnetic radiation, one of said bursts having characteristic parameters including a spectral composition, intensity, and pulse duration effective to generate, in hair shafts protruding from said skin surface, heat energy transmissible along the hair shafts to weaken the same below said skin surface, to enable breaking of the hair shafts below said skin surface,
another of said bursts having characteristic parameters including a spectral composition, intensity, and pulse duration effective to sever the hair shafts above said skin surface.

2. The method defined in claim 1 wherein the hair fibers protrude from a measurable area of said skin surface, said total energy being between approximately 0.1 Joule and approximately 100 Joules of energy per square centimeter of said skin surface.

3. The method defined in claim 2 wherein said pulses of light have a total duration between approximately 1 nanosecond and approximately 3 seconds.

4. The method defined in claim 3 wherein the light of said pulses is incoherent and includes a range of wavelengths between about approximately 200 nm and approximately 1200 nm.

5. The method defined in claim 3 wherein the light of said pulses is incoherent and includes a range of wavelengths longer than about approximately 800 nm.

6. The method defined in claim 1, further comprising delivering a second form of energy to said hair fibers to cause the same to stand away from said skin surface, the delivering of said second form of energy including an action taken from the group consisting of applying suction to said hair fibers, vibrating said skin surface, magnetizing said hair fibers, and applying an electrostatic charge to said hair fibers.

7. The method defined in claim 1 wherein the directing of the generated pulses includes reflecting said pulses from a mirror.

8. A hair treatment method comprising:
generating electromagnetic radiation having a predetermined spectral composition and a predetermined intensity in a predetermined number of pulses each having a predetermined duration, said pulses having a predetermined total energy;
directing at least a portion of the electromagnetic radiation of the generated pulses from said generator away from entering a skin surface and in a direction substantially parallel to said skin surface, to impinge on hair fibers protruding from the skin surface; and
applying a dye to the protruding hair fibers along said skin surface prior to the directing of the generated pulses.

9. A hair treatment device comprising:
a generator of electromagnetic radiation; and
optical guide componentry operatively connected to said generator so as to direct electromagnetic radiation from said generator away from entering a skin surface and in a direction substantially parallel to said skin surface, to impinge on hair fibers protruding from the skin surface,
said light guide componentry including means for directing electromagnetic radiation from said generator into said skin surface.

10. A hair treatment device comprising:
a hand-holdable casing;
a generator of electromagnetic radiation, said generator being mounted to said casing; and
at least one optical element mounted to said casing so as to direct a first portion of electromagnetic radiation produced by said generator in a direction substantially parallel to a skin surface, to impinge on hair fibers protruding from the skin surface, and to direct a second portion of the electromagnetic radiation produced by said generator into the skin surface.

11. The device defined in claim 10 wherein said optical element includes a partially reflective and partially transmissive mirror.

12. A hair treatment method comprising:
generating electromagnetic radiation;
directing a first portion of the electromagnetic radiation in a direction substantially parallel to a skin surface, to impinge on hair fibers protruding from the skin surface; and
directing a second portion of the electromagnetic radiation into the skin surface.

13. The method defined in claim 12, further comprising directing the electromagnetic radiation through a partially reflective and partially transmissive mirror to produce said first portion and said second portion.

* * * * *